(12) United States Patent
Arnold et al.

(10) Patent No.: US 6,210,986 B1
(45) Date of Patent: *Apr. 3, 2001

(54) MICROFLUIDIC CHANNEL FABRICATION METHOD

(75) Inventors: Don W. Arnold, Livermore; Joseph S. Schoeniger; Gregory F. Cardinale, both of Oakland, all of CA (US)

(73) Assignee: Sandia Corporation, Livermore, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/404,945

(22) Filed: Sep. 23, 1999

(51) Int. Cl.$^7$ .................................................. G01N 27/26
(52) U.S. Cl. ............................ 438/42; 204/450; 204/451; 204/601
(58) Field of Search ..................... 204/454, 450, 204/451, 452, 601, 603, 600, 604, 605, 180, 299, 198; 436/34, 172, 177; 213/33

(56) References Cited

U.S. PATENT DOCUMENTS

| | | | |
|---|---|---|---|
| 4,891,120 | 1/1990 | Sethi et al. | 204/299 |
| 4,908,112 | 3/1990 | Pace | 204/299 |
| 5,126,022 | 6/1992 | Soane | 204/180.1 |
| 5,571,410 | 11/1996 | Swedberg et al. | 210/198.2 |
| 5,580,523 | 12/1996 | Bard | 422/50 |
| 5,750,015 | 5/1998 | Soane | 204/454 |
| 5,755,942 * | 5/1998 | Zanzucchi et al. | 204/454 |
| 5,824,204 | 10/1998 | Jerman | 204/601 |
| 5,858,195 | 1/1999 | Ramsey | 204/601 |
| 5,885,470 | 3/1999 | Parce et al. | 216/33 |
| 5,972,710 * | 10/1999 | Weigl et al. | 436/34 |
| 6,007,690 * | 12/1999 | Nelson et al. | 204/601 |
| 6,007,775 * | 12/1999 | Yager | 422/57 |
| 6,056,860 * | 5/2000 | Amigo et al. | 204/454 |

FOREIGN PATENT DOCUMENTS

WO 98/22811    5/1998   (WO).

OTHER PUBLICATIONS

M. Stjernstrom and J. Roeraade, Method for Fabrication of Microfluidic Systems in Glass, *J. Micromechanics and Microengineering*, 8, 33–38, 1998.

V. Spiering et al.,*J. British Interplanetary Soc.*, 51 133–136, 1998.

V. Spiering et al., *SPIE*, 2882, 91–100, 1996.

* cited by examiner

*Primary Examiner*—Charles Bowers
*Assistant Examiner*—Laura M Schillinger
(74) *Attorney, Agent, or Firm*—D. A. Nissen

(57) ABSTRACT

A new channel structure for microfluidic systems and process for fabricating this structure. In contrast to the conventional practice of fabricating fluid channels as trenches or grooves in a substrate, fluid channels are fabricated as thin walled raised structures on a substrate. Microfluidic devices produced in accordance with the invention are a hybrid assembly generally consisting of three layers: 1) a substrate that can or cannot be an electrical insulator; 2) a middle layer, that is an electrically conducting material and preferably silicon, forms the channel walls whose height defines the channel height, joined to and extending from the substrate; and 3) a top layer, joined to the top of the channels, that forms a cover for the channels. The channels can be defined by photolithographic techniques and are produced by etching away the material around the channel walls.

17 Claims, 6 Drawing Sheets

MICROFLUIDIC CHANNEL FABRICATION METHOD

CROSS-REFERENCE TO RELATED APPLICATIONS

Not applicable.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention pertains generally to microfluidic structures and particularly to a microchannel structure and a method for fabricating the microchannel structure on a substrate.

The microscale devices that constitute a microfluidic system typically consist of a plurality of grooves, or microchannels, and chambers etched or molded in a substrate that can be silicon, plastic, quartz, glass, or plastic. The size, shape and complexity of these microchannels and their interconnections influence the limits of a microsystem's functionality and capabilities. In turn, the size, shape and complexity of microchannels and structures that can be used in microfluidic systems depend on the materials used and the fabrication processes available for those materials. Typical system fabrication includes making trenches in a conducting material (silicon) or in a non-conducting substrate (e.g., glass or plastic) and converting them to channels by bonding a cover plate to the substrate. The typical overall channel sizes range from about 5–100 $\mu$m wide and 5–100 $\mu$m deep.

For example, U.S. Pat. Nos. 5,885,470 teaches a microfluidic device having application in chemistry, biotechnology, and molecular biology that provides precise control of fluids by forming various grooves or channels and chambers in a polymeric substrate. The process of forming channels can include wet chemical etching, photolithographic techniques, controlled vapor deposition, and laser drilling into a substrate.

U.S. Pat. No. 5,571,410 discloses a miniaturized analysis system comprising microstructures fabricated on a non-silicon or $SiO_2$ substrate by laser ablation.

U.S. Pat. No. 5,580,523 relates to a method and apparatus for continuous synthesis of chemical compounds under controlled and regulated conditions comprising microreactors. The microreactors are fabricated by photolithographic methods, wherein a photoresist is applied to the upper surface of a Si or $SiO_2$ substrate and the microreactor and associated flow channels are etched into the substrate by an appropriate reagent.

Similar apparatus and methods of fabricating microfluidic devices are also taught and disclosed in U.S. Pat. Nos. 5,858,195, 5,126,022, 4,891,120, 4,908,112, and 5,750,015 and International PCT Application WO 98/22811.

As exemplified by the foregoing, prior art teaches typical system fabrication that includes making trenches 125 in a substrate 110 and converting the trenches to channels by bonding a cover plate 120 to the substrate, as illustrated in plan view in FIG. 1a and in cross-section in FIG. 1b. Typical overall channel sizes are on the order of 5–100 $\mu$m wide and 5–100 $\mu$m deep. However, there are significant limitations inherent in these fabrication methods, particularly with regard to aspect ratio (the ratio of channel height to width), the slope of the channel walls, and system channel dimensions, generally. By way of example, the most widely used processes include isotropic wet chemical etching of glass or silica and molding of plastics. Isotropic etching produces channels that re significantly wider at the top than at the bottom, thus limiting channel aspect ratios. In techniques requiring molding or stamping, the aspect ratio is limited by the tool removal step. Large height-to-width ratios increase the mold adhesion transverse to the molding force direction.

Due to the favorable scaling laws for electro-osmosis and electrophoresis, many microfluidic structures are designed to produce and guide electrokinetically-driven flows. Electrokinetically-driven flows require application of high voltages to a fluid contained within the patterned microchannels. Consequently, successful electtokinetic system operation requires that the substrate channels be much less electrically conductive than the liquid contained therein. While microfluidic systems can be produced directly in electrically insulating materials, the clear advantages of silicon micromachining technologies as applied to microfluidic systems have been recognized. However, a significant obstacle to the development of silicon-based Microsystems is the inability to operate at voltages required for electrokinetic separation or pumping operations (i.e., in the kV range). Prior art approaches to making silicon devices that can be used in this voltage range attempt to reduce electrical current flow through the silicon substrate by depositing insulating layers, such as $SiO_2$ and $SiN_x$, with minimal success. Very high failure rates occur because extremely high performance is required of the insulating layer. By way of example, consider the voltage gradient across an insulating layer that coats a silicon channel that contains a liquid with a voltage applied between the two ends of the channel. For successful operation, this voltage gradient must not exceed the dielectric breakdown voltage of the $SiO_2$ insulator layer. The breakdown potential gradient of pure $SiO_2$ (quartz) is about $7 \times 10^6$ V/cm. The application of 1000 V (a modest voltage for electrokinetic separation or pumping operations) to a channel in a grounded silicon microfluidic system produces a voltage gradient across a 1 $\mu$m thick $SiO_2$ layer as large as $1 \times 10^7$ V/cm. Therefore, we require an insulator having a thickness of about 10 $\mu$m to prevent dielectric breakdown from the 1000 V applied to the channel. This value of thickness of the $SiO_2$ layer assumes no pores or other defects, such as impurities, are present in the insulating layer through which current can leak. Deposition of such high quality or "defect free" layers is extremely challenging for standard thin film deposition tools. Consequently, much thicker layers must be used to withstand the larger voltages desired for electrokinetic separations or pumping applications. As a result, these coating methods place fundamental limits on the minimum size features that can be incorporated into a microfluidic system. Additionally, a high demand is placed on the structural integrity of the insulating layers because they are in contact with the fluids contained in the channels. The insulator layer integrity requirements are generally more stringent for fluidic systems than for electronics applications because the electrically charged liquid and electrolytes, by their inherent nature, will find any imperfection in the insulator layer and short circuit the system through the bulk silicon substrate. Additionally, the chemical nature of the fluids can vary over a range of pH. On the microscopic scale chemical reactions (e.g., attack of $SiO_2$ by base) can actually dissolve or produce imperfections in the insulator layers if they are not sufficiently robust.

Sealing the top plate, or cover, onto the etched substrate remains a significant practical problem in the fabrication of microfluidic systems having channels etched into the substrate. Unfortunately, while silica-based materials (crystalline and amorphous silicon dioxide and glasses) generally have good optical properties and chemical resistance and are good electrical insulators, they all have high melting temperatures. As a result, glass channel sealing processes require heating to >600° C. For quartz, a temperature in excess of 1100° C. is needed. High temperature processes limit the use of many useful designs and materials that one might want to include in a microfluidic device. For example, it is difficult for metal electrodes or surface coatings to survive the sealing process due to differential thermal expansion, or even complete evaporation, at the temperatures required for quartz bonding.

For many chemical analysis applications, such as chromatographic separations, it is necessary to have channels packed with a porous material. The porous material can either be placed into a previously fabricated channel or, preferably, the porous material can be microfabricated directly into the channel. Processes have been developed for etching silicon with a very high anisotropy and near normal sidewalls. For example, it is now possible to etch features having submicron dimensions and about 100 µm tall. Consequently, a variety of process are available for production of small-scale structures in silicon than any other material, and much smaller feature sizes can be achieved. However at present, there is no reliable way of using these small scale silicon features in microfluidic applications that require the use of very high (kV) voltages.

The deficiencies inherent in conventional methods of fabricating microchannels, particularly for electrokinetic applications, have been recognized and the use of free-standing walls to construct microchannels has been proposed. In one instance, very fragile, thin-walled silicon nitride channels can be fabricated on top of glass plates (V. Spiering et al., *J. British Interplanetary Soc.*, 51, 133–136, 1998). These structures are not conducting and thus are potentially suitable for electrokinetic applications. Moreover, it is suggested that this process provides a means to take advantage of silicon micromachining methods. However, significant inherent limitations in the technique remove most of these advantages. The nitride used has a breakdown voltage significantly less than that of glass or silica limiting the applied voltages that may be used. Also, there is no way presently to fabricate high aspect ratio features in the channels by this method.

In a second instance (M. Stjernstrom and J. Roeraade, Method for Fabrication of Microfluidic Systems in Glass, *J. Micromechanics and Microenginneering*, 8, 33–38, 1998) walls are formed that define the channels rather than simply forming trenches in the substrate. However, in this case isotropic wet glass etching is still employed and the wall-fabrication method is simply an effort to improve yield by decreasing the sensitivity of the bonding process to particulate contamination (a principle complication for thermal bonding). The process used, and the architecture defined by the process, have all the inherent limitations of glass trenches, in that the size and height of structures that may be defined in the channels is limited.

Jerman in U.S. Pat. No. 5,824,204 teaches a micromachined structure for handling fluids with an applied voltage in which fluid carrying channels are formed from silicon nitride on a non-conducting (glass) substrate. The silicon nitride channels and are formed by conformal coating etched features in a silicon wafer with deposited silicon nitride. The silicon nitride channels are bonded to the glass substrate by an intermediate thermal oxide layer grown on the surface of the silicon nitride. The silicon wafer is etched away leaving silicon nitride channels on the surface of the glass substrate. An electrically insulating material can be applied to the substrate to support the silicon nitride structures. While the structure disclosed here overcomes the disadvantages of conventional microchannel fabrication schemes, it suffers from the disadvantages discussed above. Namely, the need to limit the voltage applied because of the relatively low breakdown voltage of silicon nitride and difficulties inherent in fabricating nonporous, defect-free structures by chemical or physical deposition methods.

Accordingly, there is a need for an improved method for fabricating microchannels that is able to overcome shortcomings inherent in conventional fabrication methods while providing high-aspect-ratio microchannel structures having high-voltage compatibility, optical transparency, excellent solvent resistance and low cost.

SUMMARY OF THE INVENTION

The present invention provides a microfluidic device having a novel microchannel architecture. Microfluidic devices produced in accordance with the invention are a hybrid assembly generally consisting of three layers: 1) a substrate that can or cannot be an electrical insulator; 2) a middle layer that forms the channel walls and whose height defines the channel wall height. This layer, which is preferably high resistivity silicon, is joined, by bonding, to the substrate; and 3) a top layer, joined to the top of the channels, that forms a cover for the channels. The channels are defined by photolithographic techniques and a free-standing, thin walled channel structure is produced by etching away the material from around the channel walls.

The free-standing structures can be made to have very thin or very thick walls in relation to the channel width and height. Moreover, the sidewalls as well as the top and bottom of a channel can all be of different thickness. They can be all made of the same material, or of different materials, or a combination of materials, such as a combination of an optically transparent material (glass) and an opaque material (silicon). Sealed channels can be made entirely out of silicon with glass substrates present only for mechanical support. Thus, the thickness of the walls can be used as a design parameter. With this approach, it is possible to make the channel walls out of a conductor, and still have the large majority of electrical current flow through the conducting liquid in the channel, which has a much larger cross-sectional area. This opens up possibilities for using a larger range of materials for structures (silicon in particular), wherein fluid flow is electrokinetically-driven. Further, using the method disclosed herein it is now possible to combine optically transparent and opaque materials such as glass and silicon. Furthermore, in order to make the thin walls mechanically rigid, they can be designed and fabricated with structural reinforcements that provide strength but not electrically conductive pathways. Moreover, this process can be used to fabricate a variety of mechanically supported miniature objects with high aspect ratios. Such objects can be useful as flow guides or material supports in microfluidic and micro-chromatographic applications, or can have other uses.

BRIEF DESCRIPTION OF THE DRAWINGS

The accompanying drawings, which are incorporated in and form part of the specification, illustrate the present

DETAILED DESCRIPTION OF THE INVENTION

Figure 1A:
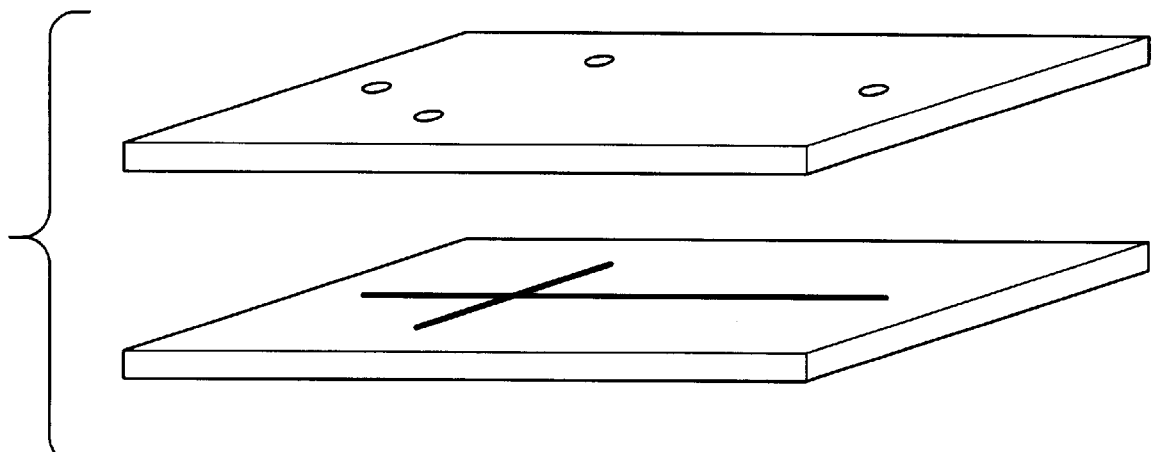
FIGS. 1a and 1b illustrate a typical prior art microchannel structure.
Figure 1B:
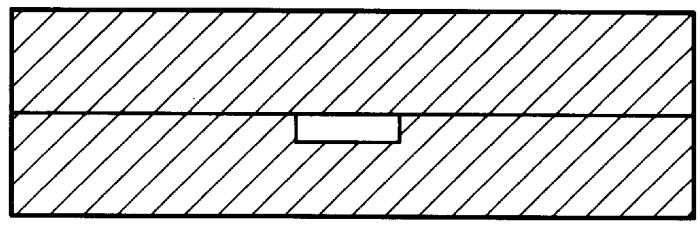

The present invention is directed toward a new channel structure for microfluidic systems and a novel process for fabricating this structure. Rather than the conventional practice of fabricating fluid channels as trenches or grooves in a substrate, fluid channels are fabricated as raised structures on a substrate.

The method of transporting fluid through the channels in a substrate, either by pressure-driven flow or electrokinetically-driven flow, i.e., fluid movement caused by the imposition of an electric field on the fluid, has conventionally determined, in part, the requisite electrical characteristics of the substrate and associated channels. If only pressure-driven flows need be accommodated, microfluidic structures can be fabricated out of any material that has the necessary characteristics of chemical compatibility and mechanical strength. Silicon is a particularly preferred material since a wide range of advanced microfabrication and micromachining techniques have been developed for it.

On the other hand, for electrokinetically-driven flows, i.e., those flows that are driven by application of a voltage to a fluid, attempts to use silicon for microfluidic devices have met with limited success. In order for a microfluidic device that employs electrokinetically-driven flows to be successful it is necessary that the medium constraining the fluid, the substrate in conventional application, be much less electrically conducting than the fluid. While microfluidic devices can be produced directly in electrically insulating materials, existing fabrication methods place lower limits on channel dimensions and particularly on the size, aspect ratio, and the slope of the channel walls. The most widely used processes include isotropic wet chemical etching of glass or silica and molding of plastics. Isotropic etching tends to produce sidewalls having a 45-degree slope. In techniques requiring molding or stamping, the aspect ratio is limited by the tool removal step. Large height-to-width ratios increase the mold adhesion force transverse to the molding force direction. These problems are overcome in the present invention since the channel walls, that now are placed on the substrate, can be either a conducting or nonconducting material, independent of the electrical characteristics of the substrate. Moreover, by providing for control of the thickness of the channel walls, it is now possible to produce very thin walled silicon channels whose conductivity is below that of the fluid.

It should be noted that throughout the written description of this invention, the terms "channel" and "microchannel" refer to structures for guiding and constraining fluid and fluid flow and will be used synonymously and interchangeably unless the context clearly declares otherwise. Further, in many applications of the invention a liquid reservoir is associated with one or more microchannels. Thus, the terms channel and microchannel include, in their broadest meaning as structures for guiding and/or constraining fluid, reservoir structures associated with microchannels. Moreover, the term "microfluidic" or "microscale" generally refers to structures or features of a device for transporting fluids that have at least one dimension or structural element in the range of from about 0.1 $\mu$m to about 500 $\mu$m.

Figure 2A:
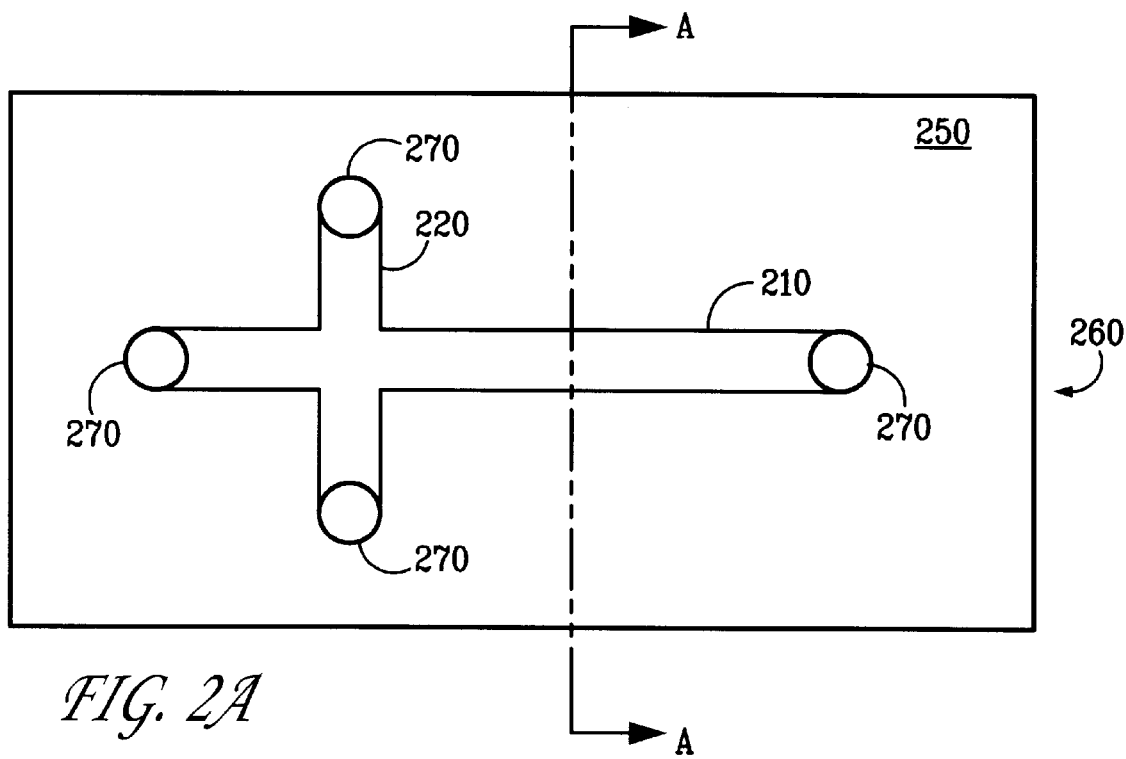
FIGS. 2a and 2b are a plan view and cross-sectional view of an embodiment of the present invention.
Figure 2B:
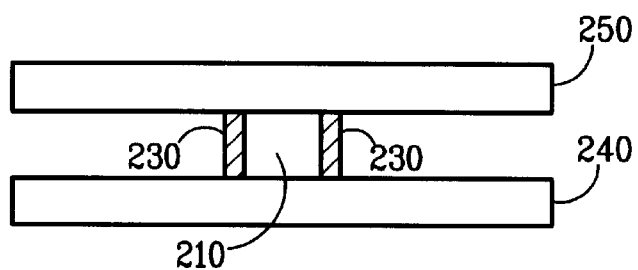

Referring now to the drawings, FIG. 2a shows a plan view of a microfluidic device 260 comprising a channel system constructed in accordance with present invention. FIG. 2b is cross-section along line A—A of FIG. 2a. Channel 210 is formed by free-standing walls 230 joined to and extending from substrate 240. Joining cover plate 250 to the top surface of walls 230 encloses channel 210. Intersecting channels 210 and 220 can be constructed as shown by FIG. 2a. Cover plate 250 has apertures 270 in communication with channels 210 and 220 that provide access means for fluids or electrodes. For the reasons discussed above, it is preferred that the channel walls be made of silicon and it is particularly preferred that they be made of silicon having a high electrical resistivity, such as float-zone silicon or silicon that is doped with dopants known to those skilled in the art, such as Au, to increase its resistivity. Because the method of fabricating the channel structure of the invention provides for controlling the thickness of the channel walls, it is possible to increase the net resistance of the silicon channel walls by making them thinner. The advantage is illustrated by the following example.

EXAMPLE

Free-standing walls, as illustrated by FIG. 2(a), are made from float-zone silicon having a resistivity of about $10^5$ ohm-cm. The walls, patterned to be 10 $\mu$m wide and 50 $\mu$m high and spaced 100 $\mu$m apart, have a cross-sectional area of about $5 \times 10^{-6}$ cm$^2$. The wall resistance along the length of the channel is then about $2 \times 10^{10}$ ohm/cm. Typically, a fluid that would be electrokinetically-driven in the channel formed by these walls (such as a commonly used 10 mM buffer solution) would have a resistivity of about $10^4$ ohm-cm. Thus, the fluid in the channel would have a resistance of about $2 \times 10^8$ ohm/cm and current would flow primarily through the fluid in the channel with only about 1% flowing through the silicon walls.

FIGS. 3a–3e illustrate a method for constructing a microfluidic device in accordance with the present invention. A substrate 240 having one flat surface is provided. The substrate can be any material that will bond to silicon, and particularly any insulating material, but Pyrex® glass is preferred and Pyrex® 7740 glass, having a coefficient of thermal expansion that is compatible with silicon, is particularly preferred. In addition to the ability to bond with silicon, other important parameters for selecting the correct substrate material are: thermal expansion coefficient compatible with silicon, flatness (or total thickness variation), and ion content.

A silicon wafer 320 is bonded to substrate 240 (FIG. 3a) by methods known to those skilled in the art, such as anodic bonding. Following the step of bonding, the thickness of the silicon wafer can be reduced to the desired height of the channel walls by chemical and/or mechanical polishing. Typically, the thickness of the silicon wafer after the polishing step is between about 20 µm to about 100 µm thick, however, thinner or thicker wafer thickness can be also accommodated. For channel walls whose height is between less than about 5 µm to about 10 µm, silicon can be directly deposited on the surface of the substrate by well known techniques such as chemical or physical vapor deposition. It should be noted that polishing of the silicon after bonding to the substrate can transfer thickness variations present in the substrate to the silicon resulting in nonuniformity of the height of the channel walls which translates into nonuniformity of the channel depth. Thus, there can be an advantage to reducing the thickness of the silicon wafer to a desired value prior to bonding to a substrate, namely improved thickness uniformity of the silicon layer. Wafers of silicon can be polished to a more uniform thickness than is generally commercially available for most substrate materials, and particularly glass.

Figure 3A:
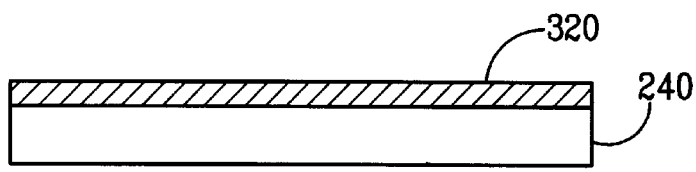
FIGS. 3a–3e are cross-sectional views of steps in a fabrication procedure for a silicon-on-glass structure.
Figure 3B:
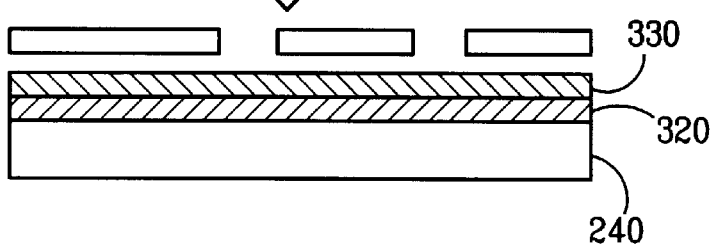
Figure 3C:
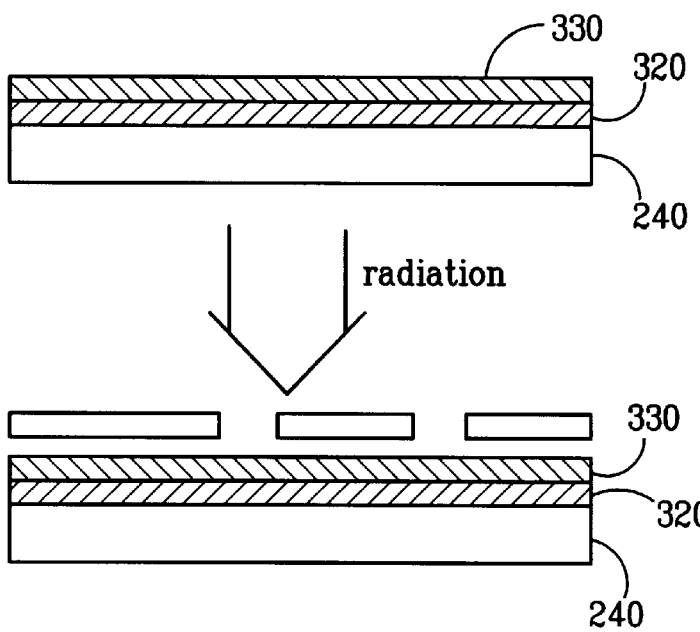
Figure 4:
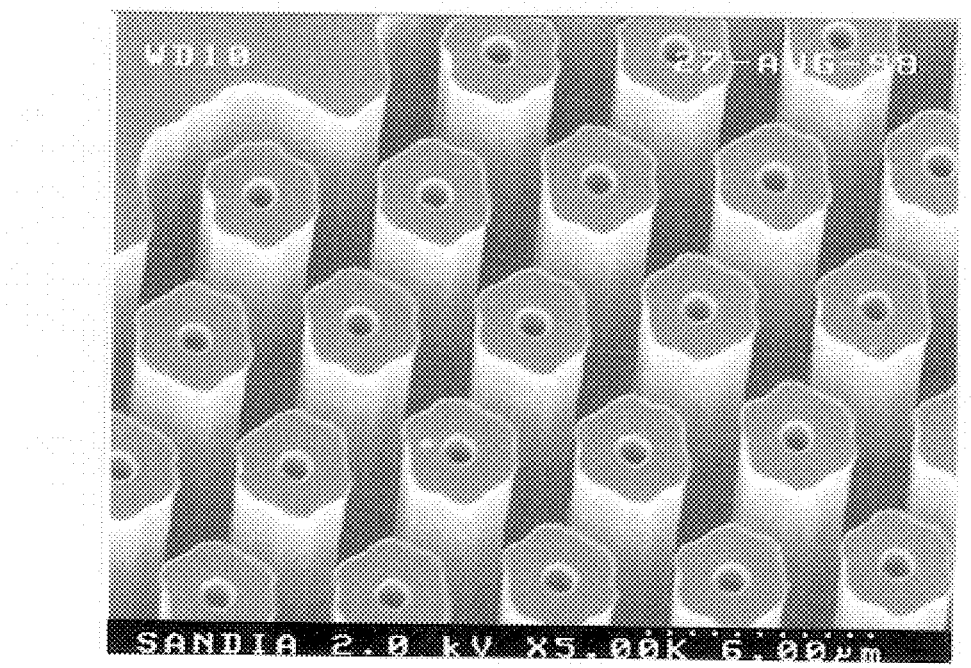
FIG. 4 shows a silicon-on-glass fabrication of a silicon post array.

An etch resistant material 330, such as polymeric photoresist material or a hard mask, such as silicon oxide, silicon nitride, or some comparable material that provides high etch selectivity for the subsequent processing step, is applied to the surface of the polished silicon layer (FIG. 3b). Photolithographic patterning methods are used to form the desired channel pattern as well as define thickness of the channel walls in the photoresist or hard mask material (FIG. 3c). Moreover, the patterning process can also be used to form structures within the channels themselves, such as those shown in FIG. 4, that can be used as flow guides, material supports, or as the porous phase for chromatographic separations. Here, a silicon post array, wherein each post 410 is 3 µm in diameter and 75 µm tall, has been fabricated on a Pyrex® 7740 glass substrate.

Figure 3D:
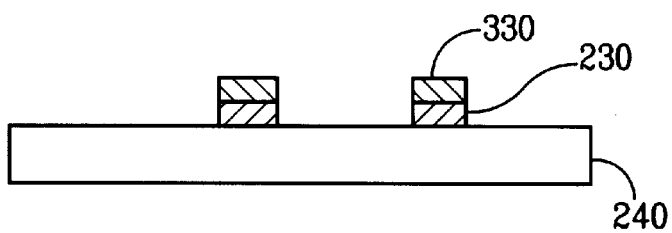
Figure 3E:
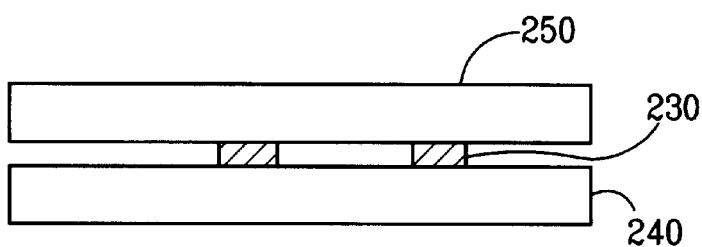

Using an etching process, such as deep reactive ion etching (DRIE), the silicon layer can be etched through its entire thickness down to the substrate that acts as an etch stop and can define the bottom of the channel (FIG. 3d). The etching process removes all the silicon not protected by the photoresist or hard mask. The result is free-standing silicon walls, such as 230, that define the microchannels themselves as well as the pattern of interconnected microchannels. It can be desirable to remove silicon by repeated mask/etch cycles or using a two mask process to leave a thin layer of silicon remaining on the surface of the substrate to provide additional stability to the walls or provide structures such as shelves on the channel walls themselves.

Following the etching process, the photoresist or hard mask material is removed by methods known in the art, such as by an oxygen plasma, and a cover plate 250 is sealed onto the silicon walls (FIG. 3e) to produce, in combination with the substrate and channel walls, a sealed channel(s) for conducting liquids; a structure similar to that shown in FIG. 2a. To aid in the sealing process, the silicon walls can include electrodes that extend from the channel walls to the edge of the cover plate. These electrodes can be used for anodic bonding of the glass cover plate to the silicon walls of the microchannels. Access means, such as holes or ports, can be drilled or patterned into the cover plate to provide access for liquids and/or electrodes. However, any operations, such as hole drilling, are preferably done prior to the step of sealing to avoid particle contamination in the microchannels. The cover plate can also be a glass-silicon heterostructure, i.e., glass having patterned silicon layers disposed thereon.

Figure 5:
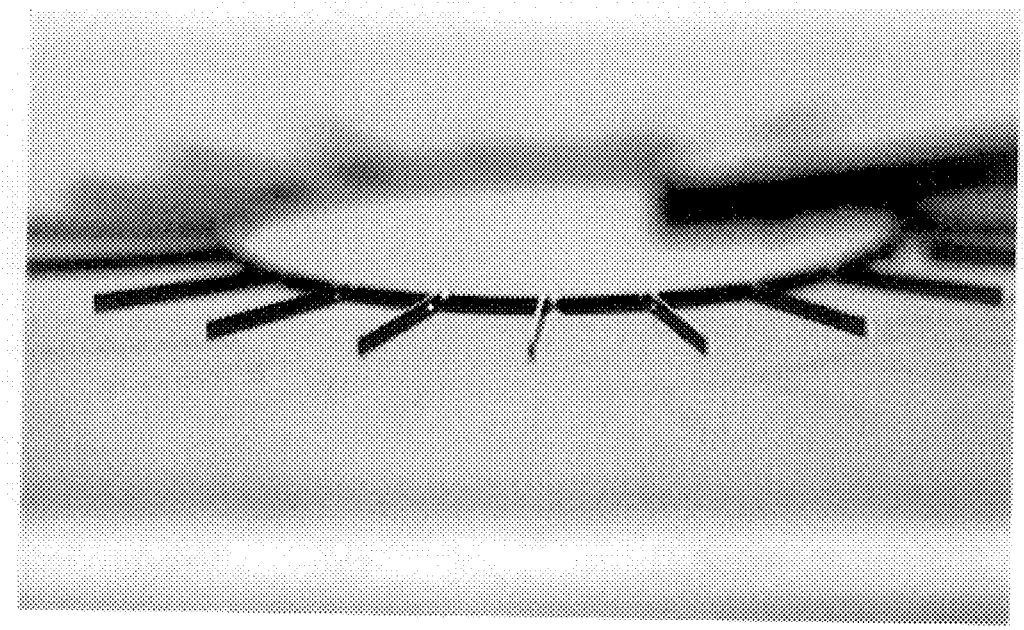
FIG. 5 is an example of a silicon-on-glass wall with supporting buttresses.
Figure 6A:
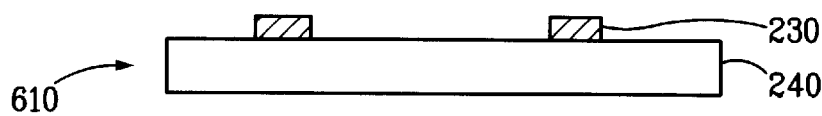
FIGS. 6a–6d are an illustration of a multilayer microfluidic device.
Figure 6B:
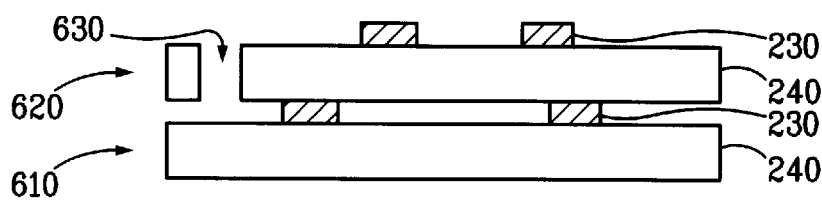
Figure 6C:
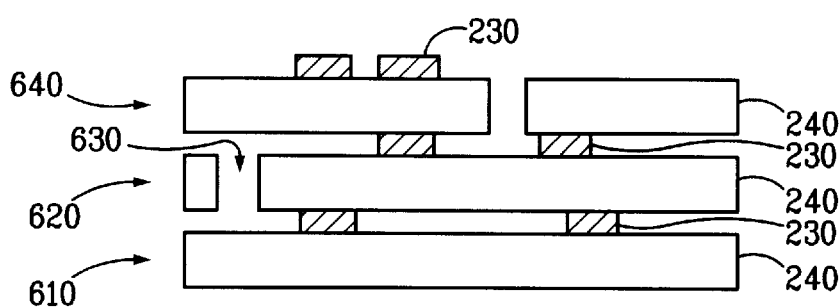
Figure 6D:
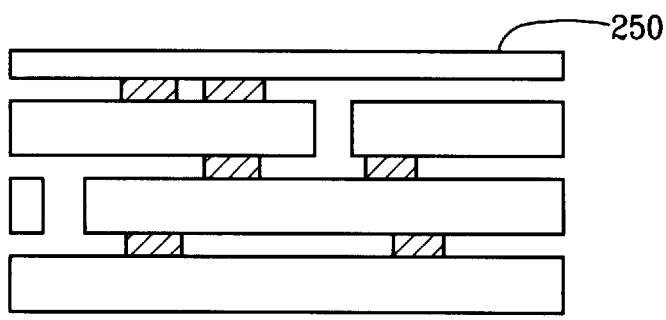

A structure made by the method of this invention is shown in FIG. 5. This is a silicon-on-glass circular wall that defines a liquid reservoir. The walls of the reservoir and supporting buttresses are 10 µm wide and 50 µm high.

It can be particularly advantageous to oxidize the silicon microchannel walls to provide a more uniform flow velocity under electrokinetically-driven operating conditions. This can be accomplished by placing the entire device into an oxidizing furnace. The oxidation can be wet or dry or by the use of high pressure oxygen. During the oxidation process it is desirable to keep the temperature below the deformation point of the substrate and cover plate, which in the case of Pyrex® 7740 glass can be about 675° C. However, the oxidation rate of silicon is slow at this temperature consequently, it can be desirable to undertake the oxidation process at elevated oxygen pressure.

For complex chemical and/or analysis schemes it can be desirable to employ a multi-layer structure in which various layers provide designated functions, requiring that these various layers be stacked one atop the other and be sealed together. By way of example, these functional layers can be a separation manifold, a fluid supply manifold, fluid waste manifold, etc.

In another aspect, the present invention provides for complex multilayer structures such as these, as illustrated in FIGS. 6a–6d. A microfluidic device comprising an array of microchannels 210 whose walls 230 extend from the surface of the substrate material 240 is prepared as described above and illustrated by FIGS. 3a–3e. This device 610 now forms the first layer in the multilayer structure. A second layer 620, having an appropriate arrangement of microchannels that can be the same or different from the first layer, is constructed in the same way and the substrate material 240 supporting this layer is joined to the microchannel walls of the first layer to form a cover plate for the first layer, forming a first array of sealed channels. This process can be repeated as many times as desired to form a plurality of layers that together forms a multilayer structure, wherein the substrate of each succeeding layer forms the cover plate for the layer immediately below. Finally, a cover plate 250 is sealed onto the silicon walls of the last layer, as described above. The arrangement of microchannels that comprise the various layers of the multilayer structure can be laid out in the same way or differently from those of the other layers. Access means 630 from one layer to the next can be drilled or patterned into the substrate material to provide access for liquids and/or electrodes.

Figure 7A:
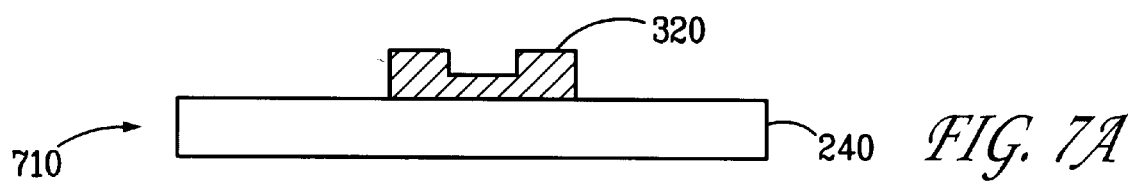
FIGS. 7a–7d illustrate a method of preparing free-standing capillary structures in accordance with the present invention.
Figure 7B:
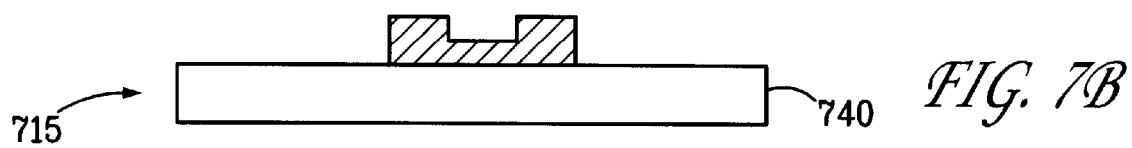
Figure 7C:
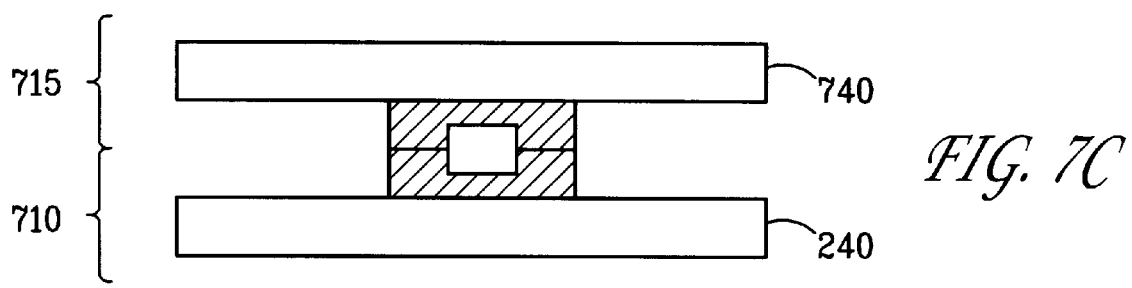
Figure 7D:
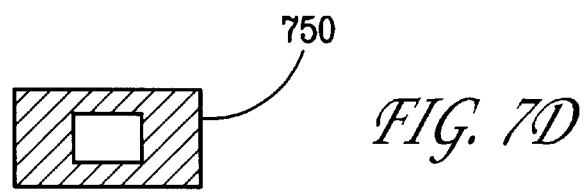

Yet another aspect of the present invention provides a method for making free-standing capillary structures. The process is illustrated by reference to FIGS. 7a–7d. As described above, one or more channel structures 710 are etched on a silicon wafer that has been bonded to a substrate 240. However, rather than etching the silicon wafer all the way through to the substrate, as above, a thin layer of silicon is left in the region between the channel walls (FIG. 7a). A channel structure 715 that can be equivalent or complementary is prepared on a second substrate 740 (FIG. 7b). The walls of the two channel structures are bonded together (FIG. 7c) by methods known to those skilled in the art to form an elongate bore having silicon walls. Finally, the substrate materials are etched away (FIG. 7d) leaving a free-standing silicon capillary structure. As illustrated, the capillary bore is angular, however, by proper control of the silicon etching process other shapes are possible. For some applications it can be desirable to have capillary structures comprising different materials. Thus, it will be obvious to those skilled in the art that the two channel structures can be made of different materials providing they can be joined together.

Another embodiment of the free-standing capillary structure disclosed above is contemplated. While FIG. 7b shows two equivalent structures that are subsequently joined together to form a capillary, other methods of forming free-standing capillary structures are within the scope of the present invention. By way of example, three sides of a capillary structure can be formed on a substrate by the method set forth above and a fourth complementary side can be formed on a second substrate and the parts subsequently joined together.

In summary, by providing a method of making walls of an electrically conducting material, preferably silicon, joined to and extending from a substrate that can be an electrical insulator or electrical conductor, to define channels in microfluidic devices, the present invention permits the use of micromachining. By controlling the dimensions of the channel-defining walls and thus the resistivity of the material used to make the walls, it is now possible to operate, for example, silicon-based microfluidic devices at the high voltages required for various electrically-driven applications such as pumps and devices for chemical analysis, synthesis, and separations without the need for a high resistivity silicon oxide or nitride coating. Moreover, the ability to use micromachining technology makes possible the incorporation of structures within the channels themselves that can be used as flow guides, material supports, or as the porous phase for chromatographic separations. It is contemplated that some microfluidic device architectures will require a multilayer structure. This complex structure can be easily accommodated by the method of the present invention, in contrast to prior art devices.

While the present invention is exemplified and illustrated by the use of silicon to fabricate channel structures it would be obvious to those of skill in the art that any electrically conducting material that can be patterned to control the dimensions of the channel defining walls and thereby their resistivity, can be used to fabricate the devices disclosed and claimed herein.

The above described methods and the arrangement of apparatus pertaining thereto are merely illustrative of applications of the principles of this invention and many other embodiments and modifications can be made by those of skill in the art without departing from the spirit and scope of the invention as defined in the claims.

We claim:

1. A microfluidic device, comprising:
    a) a substrate having an upper and a lower opposing surface;
    b) an electrically conducting material joined to the upper surface of said substrate and etched to form an array of microchannels disposed on the upper surface of said substrate, each microchannel comprising a pair of free standing walls joined to and extending from the upper surface of said substrate; and
    c) a cover plate joined to the tops of the channel walls and configured to provide access to the microchannel array.

2. The device of claim 1, wherein the electrically conducting material is silicon.

3. The device of claim 2, wherein the silicon is deposited on said substrate by chemical vapor deposition, or physical vapor deposition.

4. The device of claim 2, where the silicon has a resistivity greater than about $10^5$ ohm-cm.

5. The device of claim 1, wherein the substrate is a nonconductor of electricity.

6. The device of claim 5, wherein the substrate is a glass.

7. The device of claim 6, wherein the glass is Pyrex® 7740 glass.

8. The device of claim 1, further including structures formed within the microchannels.

9. The device of claim 1, wherein the channels are rectangular in cross section.

10. A method for fabricating a microfluidic device, comprising:
    a) providing a substrate having upper and a lower opposing faces and an electrically conducting material disposed on the upper face to form a conductor/substrate assembly;
    b) patterning a mask on the surface of the electrical conductor form a desired arrangement of channels on the electrical conductor and to define the thickness of the channel walls;
    c) etching away that part of the electrical conductor not protected by the mask to form channel walls joined to and extending from the upper face of the substrate;
    d) removing the mask; and
    e) sealing a cover plate to the tops of the channel walls to define sealed channel structures between the substrate and the cover plate, wherein the cover plate is configured to provide access to the channel structure.

11. The method of claim 10, wherein the electrically conducting material is silicon.

12. The method of claim 10, further including the step of oxidation.

13. The method of claim 10, further including the step of forming structures within the channels.

14. A microfluidic device made by the method of claim 10.

15. A microfluidic device, comprising:
    a plurality of layers joined together to form a multilayer structure, each layer comprising; a substrate having an upper and a lower opposing surface; and an electrically conducting material joined to the upper surface of said substrate and etched to form an array of microchannels disposed on the upper surface of said substrate, each microchannel comprising a pair of free standing walls joined to and extending from the upper surface of said substrate, each substrate is configured to provide access to the layer immediately below.

16. A method of forming a capillary structure, comprising:
    a) providing a substrate having upper and a lower opposing faces and having an electrically conducting material disposed on the upper face to form a first conductor/substrate assembly;
    b) providing a second conductor/substrate assembly;
    c) patterning a mask on the surface of at least one of the conductor/substrate assemblies, wherein the mask pattern and the thickness of the conductors together define the thickness of the capillary walls;
    d) etching away that part of the conductor not protected by the mask to form a channel structure joined to and extending from the substrate;
    e) aligning the structures on the first and second conductor/substrate assemblies to define an elongate bore; and
    f) joining the aligned structures.

17. The method of claim 16, further including the step of etching away at least one of the substrates.

* * * * *